United States Patent [19]
Honjo et al.

[11] Patent Number: 6,160,089
[45] Date of Patent: Dec. 12, 2000

[54] METHOD FOR SECRETORY PRODUCTION OF HUMAN GROWTH HORMONE

[75] Inventors: Masaru Honjo; Naokazu Naitoh; Hiroshi Uchida; Daisuke Mochizuki; Kazuya Matsumoto, all of Chiba, Japan

[73] Assignee: Mitsui Chemicals, Inc., Japan

[21] Appl. No.: 09/348,578

[22] Filed: Jul. 7, 1999

[30] Foreign Application Priority Data

Jul. 8, 1998 [JP] Japan ................................. 10-193003

[51] Int. Cl.⁷ .................................................. C07K 14/195
[52] U.S. Cl. ........................... 530/324; 530/326; 530/327
[58] Field of Search ..................................... 530/325, 300, 530/324; 536/23.1, 23.4; 435/69.1, 69.7, 252.3

[56] References Cited

FOREIGN PATENT DOCUMENTS 306 673   3/1989   European Pat. Off. .
587 427   3/1994   European Pat. Off. .

OTHER PUBLICATIONS

Kashiwagi K. et al.: "Identification of the polyamine–induced protein as a periplasmic oligopeptide binding protein" J. Biol. Chem., vol. 265, No. 15, May 25, 1990, pp. 8387–8391.

Van Dijl et al.: "Signal peptidase I of *Bacillus subtilis*: patterns of conserved amino acids in prokaryotic and eukaryotic type I signal peptidases" EMBO Journal, GB, Oxford University Press, Surrey, vol. 11, No. 8, Jan. 1, 1992, pp. 2819–2828.

Zhang Y–B et al.: "Analysis of a *Streptococcus pneumoniae* gene encoding signal peptidase I and overproduction of the enzyme" GENE: An International Journal On Genes And Genomes, vol. 194, No. 2, Jul. 31, 1997, pp. 249–255.

*Primary Examiner*—David Guzo
*Assistant Examiner*—Gerald G. Leffers, Jr.
*Attorney, Agent, or Firm*—Burns, Doane, Swecker, & Mathis, L.L.P.

[57] ABSTRACT

A DNA encoding 20K hGH is connected directly to a gene encoding *Escherichia coli* OppA protein secretion signal, or a modified form thereof, and a DNA encoding signal peptidase 1 to construct a recombinant plasmid, *E. coli* is transformed by said plasmid and cells of the resulting *E. coli* transformant strain are cultured for secretory production of the 20K hGH in the *E. coli* periplasm. This method enables efficient secretory production of 20K hGH and easy isolation and purification of 20K hGH from the periplasm fraction because the level of impure proteins in the *E. coli* periplasm is low.

4 Claims, 3 Drawing Sheets

Construction of pGHR52

Construction of pGHR521 to 529

Construction of pGHS525

SEQUENCE LISTING

<160> NUMBER OF SEQ ID NOS: 41

<210> SEQ ID NO 1
<211> LENGTH: 26
<212> TYPE: PRT
<213> ORGANISM: Escherichia coli
<220> FEATURE:
<221> NAME/KEY: SIGNAL
<222> LOCATION: (1)..(26)
<223> OTHER INFORMATION: Description of Artificial Sequence:OppA
                        secretion signal

<400> SEQUENCE: 1

Met Thr Asn Ile Thr Lys Arg Ser Leu Val Ala Ala Gly Val Leu Ala
 1               5                   10                  15

```
Ala Leu Met Ala Gly Asn Val Ala Leu Ala
            20                  25

<210> SEQ ID NO 2
<211> LENGTH: 27
<212> TYPE: PRT
<213> ORGANISM: Artificial Sequence
<220> FEATURE:
<223> OTHER INFORMATION: Description of Artificial Sequence:Modified
                        OppA secretion signal
<220> FEATURE:
<221> NAME/KEY: SIGNAL
<222> LOCATION: (1)..(27)

<400> SEQUENCE: 2

Met Thr Asn Ile Thr Lys Arg Ser Leu Leu Val Ala Ala Gly Val Leu
 1               5                  10                  15

Ala Ala Leu Met Ala Gly Asn Val Ala Leu Ala
            20                  25

<210> SEQ ID NO 3
<211> LENGTH: 28
<212> TYPE: PRT
<213> ORGANISM: Artificial Sequence
<220> FEATURE:
<223> OTHER INFORMATION: Description of Artificial Sequence:Modified
                        OppA secretion signal
<220> FEATURE:
<221> NAME/KEY: SIGNAL
<222> LOCATION: (1)..(28)

<400> SEQUENCE: 3

Met Thr Asn Ile Thr Lys Arg Ser Leu Leu Leu Val Ala Ala Gly Val
 1               5                  10                  15

Leu Ala Ala Leu Met Ala Gly Asn Val Ala Leu Ala
            20                  25

<210> SEQ ID NO 4
<211> LENGTH: 29
<212> TYPE: PRT
<213> ORGANISM: Artificial Sequence
<220> FEATURE:
<223> OTHER INFORMATION: Description of Artificial Sequence:Modified
                        OppA secretion signal
<220> FEATURE:
<221> NAME/KEY: SIGNAL
<222> LOCATION: (1)..(29)

<400> SEQUENCE: 4

Met Thr Asn Ile Thr Lys Arg Ser Leu Leu Leu Leu Val Ala Ala Gly
 1               5                  10                  15

Val Leu Ala Ala Leu Met Ala Gly Asn Val Ala Leu Ala
            20                  25

<210> SEQ ID NO 5
<211> LENGTH: 30
<212> TYPE: PRT
<213> ORGANISM: Artificial Sequence
<220> FEATURE:
<223> OTHER INFORMATION: Description of Artificial Sequence:Modified
                        OppA secretion signal
<220> FEATURE:
<221> NAME/KEY: SIGNAL
<222> LOCATION: (1)..(30)

<400> SEQUENCE: 5

Met Thr Asn Ile Thr Lys Arg Ser Leu Leu Leu Leu Leu Val Ala Ala
 1               5                  10                  15
```

Gly Val Leu Ala Ala Leu Met Ala Gly Asn Val Ala Leu Ala
            20                  25                  30

<210> SEQ ID NO 6
<211> LENGTH: 31
<212> TYPE: PRT
<213> ORGANISM: Artificial Sequence
<220> FEATURE:
<223> OTHER INFORMATION: Description of Artificial Sequence:Modified
      OppA secretion signal
<220> FEATURE:
<221> NAME/KEY: SIGNAL
<222> LOCATION: (1)..(31)

<400> SEQUENCE: 6

Met Thr Asn Ile Thr Lys Arg Ser Leu Leu Leu Leu Leu Val Ala
 1               5                  10                  15

Ala Gly Val Leu Ala Ala Leu Met Ala Gly Asn Val Ala Leu Ala
            20                  25                  30

<210> SEQ ID NO 7
<211> LENGTH: 32
<212> TYPE: PRT
<213> ORGANISM: Artificial Sequence
<220> FEATURE:
<223> OTHER INFORMATION: Description of Artificial Sequence:Modified
      OppA secretion signal
<220> FEATURE:
<221> NAME/KEY: SIGNAL
<222> LOCATION: (1)..(32)

<400> SEQUENCE: 7

Met Thr Asn Ile Thr Lys Arg Ser Leu Leu Leu Leu Leu Leu Val
 1               5                  10                  15

Ala Ala Gly Val Leu Ala Ala Leu Met Ala Gly Asn Val Ala Leu Ala
            20                  25                  30

<210> SEQ ID NO 8
<211> LENGTH: 33
<212> TYPE: PRT
<213> ORGANISM: Artificial Sequence
<220> FEATURE:
<221> NAME/KEY: SIGNAL
<222> LOCATION: (1)..(33)
<220> FEATURE:
<223> OTHER INFORMATION: Description of Artificial Sequence:Modified
      OppA secretion signal

<400> SEQUENCE: 8

Met Thr Asn Ile Thr Lys Arg Ser Leu Leu Leu Leu Leu Leu Leu
 1               5                  10                  15

Val Ala Ala Gly Val Leu Ala Ala Leu Met Ala Gly Asn Val Ala Leu
            20                  25                  30

Ala

<210> SEQ ID NO 9
<211> LENGTH: 34
<212> TYPE: PRT
<213> ORGANISM: Artificial Sequence
<220> FEATURE:
<221> NAME/KEY: SIGNAL
<222> LOCATION: (1)..(34)
<220> FEATURE:
<223> OTHER INFORMATION: Description of Artificial Sequence:Modified
      OppA secretion signal

<400> SEQUENCE: 9

```
    Met Thr Asn Ile Thr Lys Arg Ser Leu Leu Leu Leu Leu Leu Leu
    1               5                   10                  15
    Leu Val Ala Ala Gly Val Leu Ala Ala Leu Met Ala Gly Asn Val Ala
                    20                  25                  30
    Leu Ala
```

<210> SEQ ID NO 10
<211> LENGTH: 27
<212> TYPE: PRT
<213> ORGANISM: Artificial Sequence
<220> FEATURE:
<221> NAME/KEY: SIGNAL
<222> LOCATION: (1)..(27)
<220> FEATURE:
<223> OTHER INFORMATION: Description of Artificial Sequence:Modified
      OppA secretion signal

<400> SEQUENCE: 10

```
Met Thr Asn Ile Thr Lys Lys Arg Ser Leu Val Ala Ala Gly Val Leu
1               5                   10                  15
Ala Ala Leu Met Ala Gly Asn Val Ala Leu Ala
                20                  25
```

<210> SEQ ID NO 11
<211> LENGTH: 28
<212> TYPE: PRT
<213> ORGANISM: Artificial Sequence
<220> FEATURE:
<221> NAME/KEY: SIGNAL
<222> LOCATION: (1)..(28)
<220> FEATURE:
<223> OTHER INFORMATION: Description of Artificial Sequence:Modified
      OppA secretion signal

<400> SEQUENCE: 11

```
Met Thr Asn Ile Thr Lys Lys Arg Ser Leu Leu Val Ala Ala Gly Val
1               5                   10                  15
Leu Ala Ala Leu Met Ala Gly Asn Val Ala Leu Ala
                20                  25
```

<210> SEQ ID NO 12
<211> LENGTH: 29
<212> TYPE: PRT
<213> ORGANISM: Artificial Sequence
<220> FEATURE:
<221> NAME/KEY: SIGNAL
<222> LOCATION: (1)..(29)
<220> FEATURE:
<223> OTHER INFORMATION: Description of Artificial Sequence:Modified
      OppA secretion signal

<400> SEQUENCE: 12

```
Met Thr Asn Ile Thr Lys Lys Arg Ser Leu Leu Leu Val Ala Ala Gly
1               5                   10                  15
Val Leu Ala Ala Leu Met Ala Gly Asn Val Ala Leu Ala
                20                  25
```

<210> SEQ ID NO 13
<211> LENGTH: 30
<212> TYPE: PRT
<213> ORGANISM: Artificial Sequence
<220> FEATURE:
<221> NAME/KEY: SIGNAL
<222> LOCATION: (1)..(30)
<220> FEATURE:
<223> OTHER INFORMATION: Description of Artificial Sequence:Modified
      OppA secretion signal

```
<400> SEQUENCE: 13

Met Thr Asn Ile Thr Lys Lys Arg Ser Leu Leu Leu Val Ala Ala
 1               5                  10                  15

Gly Val Leu Ala Ala Leu Met Ala Gly Asn Val Ala Leu Ala
            20                  25                  30

<210> SEQ ID NO 14
<211> LENGTH: 31
<212> TYPE: PRT
<213> ORGANISM: Artificial Sequence
<220> FEATURE:
<221> NAME/KEY: SIGNAL
<222> LOCATION: (1)..(31)
<220> FEATURE:
<223> OTHER INFORMATION: Description of Artificial Sequence:Modified
      OppA secretion signal

<400> SEQUENCE: 14

Met Thr Asn Ile Thr Lys Lys Arg Ser Leu Leu Leu Leu Val Ala
 1               5                  10                  15

Ala Gly Val Leu Ala Ala Leu Met Ala Gly Asn Val Ala Leu Ala
            20                  25                  30

<210> SEQ ID NO 15
<211> LENGTH: 32
<212> TYPE: PRT
<213> ORGANISM: Artificial Sequence
<220> FEATURE:
<221> NAME/KEY: SIGNAL
<222> LOCATION: (1)..(32)
<220> FEATURE:
<223> OTHER INFORMATION: Description of Artificial Sequence:Modified
      OppA secretion signal

<400> SEQUENCE: 15

Met Thr Asn Ile Thr Lys Lys Arg Ser Leu Leu Leu Leu Leu Val
 1               5                  10                  15

Ala Ala Gly Val Leu Ala Ala Leu Met Ala Gly Asn Val Ala Leu Ala
            20                  25                  30

<210> SEQ ID NO 16
<211> LENGTH: 33
<212> TYPE: PRT
<213> ORGANISM: Artificial Sequence
<220> FEATURE:
<221> NAME/KEY: SIGNAL
<222> LOCATION: (1)..(33)
<220> FEATURE:
<223> OTHER INFORMATION: Description of Artificial Sequence:Modified
      OppA secretion signal

<400> SEQUENCE: 16

Met Thr Asn Ile Thr Lys Lys Arg Ser Leu Leu Leu Leu Leu Leu
 1               5                  10                  15

Val Ala Ala Gly Val Leu Ala Ala Leu Met Ala Gly Asn Val Ala Leu
            20                  25                  30

Ala

<210> SEQ ID NO 17
<211> LENGTH: 34
<212> TYPE: PRT
<213> ORGANISM: Artificial Sequence
<220> FEATURE:
<221> NAME/KEY: SIGNAL
<222> LOCATION: (1)..(34)
<220> FEATURE:
```

```
<223> OTHER INFORMATION: Description of Artificial Sequence:Modified
                      OppA secretion signal

<400> SEQUENCE: 17

Met Thr Asn Ile Thr Lys Lys Arg Ser Leu Leu Leu Leu Leu Leu
  1               5                  10                  15

Leu Val Ala Ala Gly Val Leu Ala Ala Leu Met Ala Gly Asn Val Ala
             20                  25                  30

Leu Ala

<210> SEQ ID NO 18
<211> LENGTH: 35
<212> TYPE: PRT
<213> ORGANISM: Artificial Sequence
<220> FEATURE:
<221> NAME/KEY: SIGNAL
<222> LOCATION: (1)..(35)
<220> FEATURE:
<223> OTHER INFORMATION: Description of Artificial Sequence:Modified
                      OppA secretion signal

<400> SEQUENCE: 18

Met Thr Asn Ile Thr Lys Lys Arg Ser Leu Leu Leu Leu Leu Leu
  1               5                  10                  15

Leu Leu Val Ala Ala Gly Val Leu Ala Ala Leu Met Ala Gly Asn Val
             20                  25                  30

Ala Leu Ala
         35

<210> SEQ ID NO 19
<211> LENGTH: 28
<212> TYPE: PRT
<213> ORGANISM: Artificial Sequence
<220> FEATURE:
<221> NAME/KEY: SIGNAL
<222> LOCATION: (1)..(28)
<220> FEATURE:
<223> OTHER INFORMATION: Description of Artificial Sequence:Modified
                      OppA secretion signal

<400> SEQUENCE: 19

Met Thr Asn Ile Thr Lys Lys Lys Arg Ser Leu Val Ala Ala Gly Val
  1               5                  10                  15

Leu Ala Ala Leu Met Ala Gly Asn Val Ala Leu Ala
             20                  25

<210> SEQ ID NO 20
<211> LENGTH: 29
<212> TYPE: PRT
<213> ORGANISM: Artificial Sequence
<220> FEATURE:
<221> NAME/KEY: SIGNAL
<222> LOCATION: (1)..(29)
<220> FEATURE:
<223> OTHER INFORMATION: Description of Artificial Sequence:Modified
                      OppA secretion signal

<400> SEQUENCE: 20

Met Thr Asn Ile Thr Lys Lys Lys Arg Ser Leu Leu Val Ala Ala Gly
  1               5                  10                  15

Val Leu Ala Ala Leu Met Ala Gly Asn Val Ala Leu Ala
             20                  25

<210> SEQ ID NO 21
<211> LENGTH: 30
```

```
<212> TYPE: PRT
<213> ORGANISM: Artificial Sequence
<220> FEATURE:
<221> NAME/KEY: SIGNAL
<222> LOCATION: (1)..(30)
<220> FEATURE:
<223> OTHER INFORMATION: Description of Artificial Sequence:Modified
                        OppA secretion signal

<400> SEQUENCE: 21

Met Thr Asn Ile Thr Lys Lys Lys Arg Ser Leu Leu Leu Val Ala Ala
 1               5                  10                  15

Gly Val Leu Ala Ala Leu Met Ala Gly Asn Val Ala Leu Ala
            20                  25                  30

<210> SEQ ID NO 22
<211> LENGTH: 31
<212> TYPE: PRT
<213> ORGANISM: Artificial Sequence
<220> FEATURE:
<221> NAME/KEY: SIGNAL
<222> LOCATION: (1)..(31)
<220> FEATURE:
<223> OTHER INFORMATION: Description of Artificial Sequence:Modified
                        OppA secretion signal

<400> SEQUENCE: 22

Met Thr Asn Ile Thr Lys Lys Lys Arg Ser Leu Leu Leu Leu Val Ala
 1               5                  10                  15

Ala Gly Val Leu Ala Ala Leu Met Ala Gly Asn Val Ala Leu Ala
            20                  25                  30

<210> SEQ ID NO 23
<211> LENGTH: 32
<212> TYPE: PRT
<213> ORGANISM: Artificial Sequence
<220> FEATURE:
<221> NAME/KEY: SIGNAL
<222> LOCATION: (1)..(32)
<220> FEATURE:
<223> OTHER INFORMATION: Description of Artificial Sequence:Modified
                        OppA secretion signal

<400> SEQUENCE: 23

Met Thr Asn Ile Thr Lys Lys Lys Arg Ser Leu Leu Leu Leu Leu Val
 1               5                  10                  15

Ala Ala Gly Val Leu Ala Ala Leu Met Ala Gly Asn Val Ala Leu Ala
            20                  25                  30

<210> SEQ ID NO 24
<211> LENGTH: 33
<212> TYPE: PRT
<213> ORGANISM: Artificial Sequence
<220> FEATURE:
<221> NAME/KEY: SIGNAL
<222> LOCATION: (1)..(33)
<220> FEATURE:
<223> OTHER INFORMATION: Description of Artificial Sequence:Modified
                        OppA secretion signal

<400> SEQUENCE: 24

Met Thr Asn Ile Thr Lys Lys Lys Arg Ser Leu Leu Leu Leu Leu Leu
 1               5                  10                  15

Val Ala Ala Gly Val Leu Ala Ala Leu Met Ala Gly Asn Val Ala Leu
            20                  25                  30

Ala
```

-continued

```
<210> SEQ ID NO 25
<211> LENGTH: 34
<212> TYPE: PRT
<213> ORGANISM: Artificial Sequence
<220> FEATURE:
<221> NAME/KEY: SIGNAL
<222> LOCATION: (1)..(34)
<220> FEATURE:
<223> OTHER INFORMATION: Description of Artificial Sequence:Modified
                        OppA secretion signal

<400> SEQUENCE: 25

Met Thr Asn Ile Thr Lys Lys Lys Arg Ser Leu Leu Leu Leu Leu Leu
 1               5                  10                  15

Leu Val Ala Ala Gly Val Leu Ala Ala Leu Met Ala Gly Asn Val Ala
            20                  25                  30

Leu Ala

<210> SEQ ID NO 26
<211> LENGTH: 35
<212> TYPE: PRT
<213> ORGANISM: Artificial Sequence
<220> FEATURE:
<221> NAME/KEY: SIGNAL
<222> LOCATION: (1)..(35)
<220> FEATURE:
<223> OTHER INFORMATION: Description of Artificial Sequence:Modified
                        OppA secretion signal

<400> SEQUENCE: 26

Met Thr Asn Ile Thr Lys Lys Lys Arg Ser Leu Leu Leu Leu Leu Leu
 1               5                  10                  15

Leu Leu Val Ala Ala Gly Val Leu Ala Ala Leu Met Ala Gly Asn Val
            20                  25                  30

Ala Leu Ala
        35

<210> SEQ ID NO 27
<211> LENGTH: 36
<212> TYPE: PRT
<213> ORGANISM: Artificial Sequence
<220> FEATURE:
<221> NAME/KEY: SIGNAL
<222> LOCATION: (1)..(36)
<220> FEATURE:
<223> OTHER INFORMATION: Description of Artificial Sequence:Modified
                        OppA secretion signal

<400> SEQUENCE: 27

Met Thr Asn Ile Thr Lys Lys Lys Arg Ser Leu Leu Leu Leu Leu Leu
 1               5                  10                  15

Leu Leu Leu Val Ala Ala Gly Val Leu Ala Ala Leu Met Ala Gly Asn
            20                  25                  30

Val Ala Leu Ala
        35

<210> SEQ ID NO 28
<211> LENGTH: 80
<212> TYPE: DNA
<213> ORGANISM: Artificial Sequence
<220> FEATURE:
<222> LOCATION: (1)..(80)
<223> OTHER INFORMATION: Description of Artificial Sequence:DNA sequence
                        for PCR to produce a DNA fragment having a
                        promoter of B.
                        amyloiquefaciens and the first half part of
```

OppA secretion signal

<400> SEQUENCE: 28
ttcgagctcg gtacccggag tctagtttta tattgcagaa tgcgagattg ctggtttatt    60
atacaatata agttttcatt    80

<210> SEQ ID NO 29
<211> LENGTH: 83
<212> TYPE: DNA
<213> ORGANISM: Artificial Sequence
<220> FEATURE:
<222> LOCATION: (1)..(83)
<223> OTHER INFORMATION: Description of Artificial Sequence:DNA sequence
      for PCT to produce a DNA fragment having a
      promoter of B.
      amyloiquefaciens and the first half part of
      OppA secretion signal

<400> SEQUENCE: 29
cgcctgcagc tactaaactt ctcttggtga tgttggtcat atgaaatccc cctttttgaa    60
aataatgaaa acttatattg tat    83

<210> SEQ ID NO 30
<211> LENGTH: 14
<212> TYPE: DNA
<213> ORGANISM: Artificial Sequence
<220> FEATURE:
<222> LOCATION: (1)..(14)
<223> OTHER INFORMATION: Description of Artificial Sequence:Designed DNA
      sequence to act as a primer for PCR to produce
      the latter half of OppA secretion signal hormone

<400> SEQUENCE: 30
aatttaactg tgat    14

<210> SEQ ID NO 31
<211> LENGTH: 76
<212> TYPE: DNA
<213> ORGANISM: Artificial Sequence
<220> FEATURE:
<222> LOCATION: (1)..(76)
<223> OTHER INFORMATION: Description of Artificial Sequence:Designed DNA
      sequence to act as a primer for PCR to produce
      the latter half of OppA secretion signal

<400> SEQUENCE: 31
gtagctgcag gcgttctggc tgcgctaatg gcagggaatg tcgcgctggc attcccaact    60
ataccacttt cgcgcc    76

<210> SEQ ID NO 32
<211> LENGTH: 15
<212> TYPE: DNA
<213> ORGANISM: Artificial Sequence
<220> FEATURE:
<222> LOCATION: (1)..(15)
<223> OTHER INFORMATION: Description of Artificial Sequence:Designed DNA
      sequence to act as a primer for PCR to produce
      a DNA fragment having a promoter of B.
      amyloliquefaciens and a modified first half part
      of OppA secretion signal

<400> SEQUENCE: 32 tgcaaccttta tccgc    15

<210> SEQ ID NO 33
<211> LENGTH: 45

```
<210> SEQ ID NO 33
<211> LENGTH: 45
<212> TYPE: DNA
<213> ORGANISM: Artificial Sequence
<220> FEATURE:
<222> LOCATION: (1)..(45)
<223> OTHER INFORMATION: Description of Artificial Sequence:Designed DNA
                        sequence to act as a primer for PCR to produce
                        a DNA fragment having a promoter of B.
                        amyloliquefaciens and a modified first half
                        part of OppA secretion signal

<400> SEQUENCE: 33
gcctgcagct accagacttc ttttcttttt ggtgatgttg gtcat                45

<210> SEQ ID NO 34
<211> LENGTH: 51
<212> TYPE: DNA
<213> ORGANISM: Artificial Sequence
<220> FEATURE:
<222> LOCATION: (1)..(51)
<223> OTHER INFORMATION: Description of Artificial Sequence:Designed DNA
                        sequence to act as a primer for PCR to produce
                        a DNA fragment having a promoter of B.
                        amyloliquefaciens and a modified first half
                        part of OppA secretion signal

<400> SEQUENCE: 34
gcctgcagct accaataaca gacttctttt cttttggtg atgttggtca t           51

<210> SEQ ID NO 35
<211> LENGTH: 57
<212> TYPE: DNA
<213> ORGANISM: Artificial Sequence
<220> FEATURE:
<222> LOCATION: (1)..(57)
<223> OTHER INFORMATION: Description of Artificial Sequence:Designed DNA
                        sequence to act as a primer for PCR to produce
                        a DNA fragment having a promoter of B.
                        amyloliquefaciens and a modified first half
                        part of OppA secretion signal

<400> SEQUENCE: 35
gcctgcagct accaggagca ataacagact tcttttcttt ttggtgatgt tggtcat    57

<210> SEQ ID NO 36
<211> LENGTH: 63
<212> TYPE: DNA
<213> ORGANISM: Artificial Sequence
<220> FEATURE:
<222> LOCATION: (1)..(63)
<223> OTHER INFORMATION: Description of Artificial Sequence:Designed DNA
                        sequence to act as a primer for PCR to produce
                        a DNA fragment having a promoter of B.
                        amyloliquefaciens and a modified first half
                        part of OppA secretion signal

<400> SEQUENCE: 36
gcctgcagct acgagcagca ggagcaataa cagacttctt ttcttttttgg tgatgttggt   60 cat                                                              63

<210> SEQ ID NO 37
<211> LENGTH: 69
<212> TYPE: DNA
<213> ORGANISM: Artificial Sequence
<220> FEATURE:
<222> LOCATION: (1)..(69)
<223> OTHER INFORMATION: Description of Artificial Sequence:Designed DNA
                        sequence to act as a primer for PCR to produce
                        a DNA fragment having a promoter of B.
                        amyloliquefaciens and a modified first half
                        Part of OppA secretion signal
```

<400> SEQUENCE: 37
gcctgcagct accagcagga gcagcaggag caataacaga cttcttttct ttttggtgat    60
gttggtcat                                                            69

<210> SEQ ID NO 38
<211> LENGTH: 54
<212> TYPE: DNA
<213> ORGANISM: Artificial Sequence
<220> FEATURE:
<222> LOCATION: (1)..(54)
<223> OTHER INFORMATION: Description of Artificial Sequence:Designed DNA
                        sequence to act as a primer for PCR to produce
                        a DNA fragment having a promoter of B.
                        amyloliquefaciens and a modified first half
                        part of OppA secretion signal

<400> SEQUENCE: 38
gcctgcagct acgagcaata acagacttct tttcttttg gtgatgttgg tcat           54

<210> SEQ ID NO 39
<211> LENGTH: 60
<212> TYPE: DNA
<213> ORGANISM: Artificial Sequence
<220> FEATURE:
<222> LOCATION: (1)..(60)
<223> OTHER INFORMATION: Description of Artificial Sequence:Designed DNA
                        sequence to act as a primer for PCR to produce
                        a DNA fragment having a promoter of B.
                        amyloliquefaciens and a modified first half
                        part of OppA secretion signal

<400> SEQUENCE: 39
gcctgcagct accagcagga gcaataacag acttcttttc ttttggtga tgttggtcat     60

<210> SEQ ID NO 40
<211> LENGTH: 30
<212> TYPE: DNA
<213> ORGANISM: Artificial Sequence
<220> FEATURE:
<222> LOCATION: (1)..(30)
<223> OTHER INFORMATION: Description of Artificial Sequence:Designed
                        DNA sequence to act as a primer for PCR to
                        produce a DNA fragment encoding signal
                        peptidase 1.

<400> SEQUENCE: 40
ttccaattga tggcgaatat gtttgccctg                                     30

<210> SEQ ID NO 41
<211> LENGTH: 30
<212> TYPE: DNA
<213> ORGANISM: Artificial Sequence
<220> FEATURE:
<222> LOCATION: (1)..(30)
<223> OTHER INFORMATION: Description of Artificial Sequence:Designed DNA
                        sequence to act as a primer for PCR to produce
                        a DNA fragment encoding signal peptidase 1.

<400> SEQUENCE: 41
tttctgcagt taatggatgc cgccaatgcg                                     30

METHOD FOR SECRETORY PRODUCTION OF HUMAN GROWTH HORMONE

FIELD OF THE INVENTION

The present invention relates to a method for secretory production of a human growth hormone having a molecular weight of about 20,000 using *Escherichia cole*. In particular, the present invention relates to a method for the production of growth hormone having a molecular weight of about 20,000, wherein *E. coli* is transformed by a recombinant plasmid carrying a DNA fragment in which the 5' end of a DNA fragment coding for a human growth hormone having a molecular weight of about 20,000 is linked in series to the 3' end of a DNA fragment coding for *E. coli* or Salmonella OppA secretion signal, or an amino acid modified form of *E. coli* OppA secretion signal, the resultant *E. coli* transformants are cultured, then the resultant culture fluid, cells or processed material thereof are used for the production.

Furthermore, the present invention relates to a method of producing a human growth hormone having a molecular weight of about 20,000, wherein *E. coli* is transformed with a recombinant plasmid carrying a DNA fragment coding for a human growth hormone having a molecular weight of about 20,000 and a DNA fragment coding for *E. coli* signal peptidase 1, the resulting *E. coli* transformants are cultured, then the resulting culture fluid, cells or processed materials thereof are used for the production.

Furthermore, the present invention relates to a method for increasing the production of a human growth hormone having a molecular weight of about 20,000 by altering the medium composition in culturing the transformants transformed by a recombinant plasmid with the abovementioned structure.

DESCRIPTION OF THE RELATED ART

There are two known types of human growth hormone (hGH) derived from the pituitary gland: one having a molecular weight of about 22,000 (hereinafter referred to as 22K hGH) and the other having a molecular weight of about 20,000 (hereinafter referred to as 20K hGH).

22K hGH is used for manufacturing pharmaceutical products, by means of recombinant DNA technology, for the treatment of pituitary dwarfism, pediatric chronic renal failure or the like. hGH has recently been found to have excellent activities such as immune promoting activity or lipolysis stimulating activity, as well as growth promoting activity. Broader applications are greatly expected in the future.

On the other hand, recently, the risks of side effects in the clinical use of 22K hGH are widely reported and have become important issues in securing the safety of GH in clinical use and in broadening its applications. Risks arising from the use of 22K hGH reported to date include possibilities of inducing leukemia and causing diabetes. There is a need for a growth hormone with a lower risk of side effects if its clinical applications are to be broadened.

20K hGH has an amino acid sequence which corresponds to that of 22K hGH consisting of 191 amino acids except that 15 amino acid residues from the 32nd to the 46th inclusive from the N-terminal of 22K hGH are lacked. As compared to 22K hGH, this 20K hGH is reportedly low in leukemia cell proliferation activity and glucose intolerance, which is an index of diabetogenicity. Thus, the risks of side effects reported for 22K hGH are found to be less likely with 20K hGH. Also, according to results of in vitro experiments, 20K hGH has recently been found to be different from 22K hGH in its mode of binding to GH receptors. That is, M. Wada et al. revealed the difference between the two hGHs, showing that the binding activity of 22K hGH to a GH receptor decreases on the cell surface because 22K hGH binds to GH binding protein (GH receptor outer membrane protein ) present in the serum at the level of physiological concentration, while a reduction in binding activity of 20K hGH to a GH receptor does not occur because 20K hGH hardly binds to a GH binding protein in physiological conditions, and that in a 1:2 complex (complex of 1 mole of growth hormone and 2 moles of GH receptor), which is necessary for the action of growth hormone via the GH receptor, 22K hGH forms a 1:1 complex (inactive type) while 20K hGH forms a 1:2 complex (active type) with the GH receptor (Mol. Endo 12, 1, 146–156, 1997). From these results, it is expected that 20K hGH may have higher activity than 22K hGH. It has also been revealed that as to lipolysis stimulating activity, which to date was not clear, 20K hGH is as active as 22K hGH (Japanese Patent Laid-open (Kokai) No. 97/216832, or European Patent Publication No. 0753307).

As mentioned above, 20K hGH has been found to be a growth hormone which exhibits lower risks and higher activity than 22K hGH and has become a novel growth hormone expected to be useful as a pharmaceutical product.

Recent developments in recombinant DNA technology makes it possible to produce heterologous proteins using microorganisms as host organisms. Generally, intracellular expression methods and secretory production methods are used for the production of proteins using microorganisms. In intracellular expression methods, proteins carrying methionine at the N-terminal are accumulated in the cytoplasm. In order to obtain proteins without the methionine residue at the N-terminal, it is necessary to enzymatically cleave amino acid sequences containing the methionine residue at the N-terminal, for example, by a peptidase. Further, proteins obtained by the intracellular expression methods are not active forms in their steric configurations and require refolding. Thus, intracellular expression methods are not necessarily recommended as efficient methods for protein production.

On the other hand, in secretory production methods using *E. coli*, target proteins are secreted and accumulated in the periplasm. Purification of proteins from the periplasm extract is easy because the level of impure proteins is lower than that in intracellular expression methods. Moreover, the secreted proteins have no methionine at the N-terminal and are naturally active forms in their steric configuration. Thus, secretory production methods are excellent.

However, secretory production methods using microorganisms require highly sophisticated techniques and thus rarely applied on an industrial scale. That is because precursor proteins synthesized in the cytoplasm pass through the cell membrane and because secretion signals have to be properly cleaved and removed by processing.

As to protein secretion in microorganisms, its mechanisms, relevant factors and their functions have been revealed. Based on these findings, various attempts have been made for efficient secretion methods.

Secretion signals are the first to be discussed. Secretion signals have an extremely important role in protein secretion to lead target proteins to the cytoplasmic membrane. It has been revealed that for the action of secretion signals, a positive charge in the positive charge region of their N terminals and hydrophobicity in the central hydrophobic area are essential (J. Biol. Chem., 267, 4882–4888, 1992). Based on this finding on structural characteristics of secretion signals, Udaka et al. made a modification in which a basic amino acid (Arg) was added to the N terminal positive charge region of a secretion signal of MWP (middle wall protein) derived from Bacillus brevis and a hydrophobic amino acid (Leu) was added to the central hydrophobic region in secretory production using *Bacillus brevis* as a host, and reported that the secretion efficiency of a sole fish growth hormone was improved to the level of 60 mg/L (Nippon Nogeikagaku Kaishi, 67(3), 372, 1993).

However, there are no theoretical guidelines for the modification of amino acid sequences of secretion signals and at present, preferable sequences have to be found by a try-and-error process. Further, there is no clear principle at present as to how to choose secretion signals derived from secretory proteins for target proteins for secretory production and thus, suitable secretion signals have to be found for the individual target proteins for secretory production.

The abovementioned problems are understood, for example, from the description in Japanese Patent Laid-open (kokai) No. 296491/94. It describes that the secretion signal derived from alkali phosphatase or enterotoxin, which are effective in secretory production of 22K hGH, is not necessarily effective in secretory production of several kinds of eukaryotic proteins. Namely, it reports that there were cases where no protein was synthesized, or proteins were expressed in the cytoplasm but the precursor proteins remained in the cytoplasm and not secreted depending on the combination of secretion signal and secretory protein.

Thus, it is necessary to select secretion signals appropriate to individual secretory proteins; however, to date, no secretion signal usable for secretion of any proteins has been found.

Secondly, the use of co-expression of proteins for the improvement of secretory production is discussed. To date, improvements in secretory production of proteins other than GH were reported, for example, for interleukin 6 by co-expression of SecE and prlA4 (a variant protein of SecY) (BIO/TECHNOLOGY, 12, 178–180, 1994) and human granulocyte-colony stimulating factor (G-CSF) by co-expression of a chaperon protein (Biochem. Biophys. Res. Commun., 210(2), 524–529, 1995).

As to secretory production of 20K hGH, a method in which glutathione reductase is co-expressed with 20K hGH (Japanese Patent Laid-open (Kokai) No. 322586/96; European Patent Publication No. 0735140), and a method in which *E. coli* Sec protein is co-expressed with 20K hGH (Japanese patent Laid-open (Kokai) No. 313191/97; European Patent Publication No. 0798380) were reported.

SUMMARY OF THE INVENTION

The method for the production of 20K hGH by co-expression with glutathione reductase according to the abovementioned Japanese Patent (Kokai) Laid-open No. 322586/96 (or European Patent Publication No. 0735140) enabled the production of about 70 mg per 1 L of culture fluid. However, higher productivity is desired.

Although productivity of secretory production was thus improved by co-expression with glutathione reductase, studies by the present inventors revealed that in this method, a considerable amount of impure proteins other than the target protein, 20K hGH, is contained in the perislasm fluid extract obtained from the cells by an osmotic pressure shock method. As a result, purification of 20K hGH from the periplasm fluid extract comprises many steps, which will result in high production costs to purify 20K hGH to a medically acceptable grade.

An objective of the present invention is to provide a more efficient method for secretory production of 20K hGH using microorganisms, and another objective of the present invention is to provide a method for secretory production of 20K hGH using microorganisms, in which the level of impure proteins present in the periplasm fluid extract is decreased.

Objects of the present invention are to provide plasmids containing a DNA fragment in which the 5' end of DNA encoding 20K hGH links to the 3' end of DNA encoding a secretion signal which is a modified secretion signal of *E. coli* OppA, to provide *E. coli* transformants transformed by said plasmids, and to provide a method for secretory production of 20K hGH using said *E. coli* transformants.

Other objects of the present invention are to provide a recombinant plasmid having a DNA encoding 20K hGH and a DNA encoding *E. coli* signal peptidase 1, *E. coli* transformants transformed with said plasmid, and a method for secretory production of 20K hGH using said *E. coli* transformants.

To achieve the abovementioned objectives, the present inventors tried to modify a known strain described in Japanese Patent Laid-open (Kokai) No. 322586/96 (or European Patent Publication No. 0735140), i.e., an *E. coli* transformant, MT-10765 (FERM BP-5020), which is capable of secretory production of 20K hGH using a modified secretion signal derived from a neutral protease of *Bacillus amyloliquefaciens* as a secretion signal and glutathione reductase derived from *E. coli* as a co-expression protein.

First, new secretion signals which could provide more efficient secretory production of 20K hGH were studied.

In order to confirm the effectiveness of new secretion signals, it is necessary to confirm their effect on the amount of secretory production of 20K hGH. The confirmation procedure comprises steps of constructing plasmids each containing a DNA fragment in which the 3' end of a DNA encoding a different secretion signal is connected to the 5' terminal of a DNA encoding 20K hGH, isolating *E. coli* cells transformed by said plasmids, culturing the resulting transformants, then measuring the secretory production of 20K hGH.

The present inventors attempted to increase productivity of 20K hGH by using secretion signals of proteins which are secreted in abundance in microorganisms. However, the inventors could not find secretion signals producing 20K hGH more efficiently by this method than by conventional methods.

Protein secretion is a physicochemical phenomenon in which proteins pass through the cell membrane in an energy-dependent manner. Therefore, the present inventors hypothesized that use of a secretion signal of a protein which is highly homologous to 20K hGH in its structure might be preferable. A protein having an amino acid composition highly homologous to 20K hGH and a protein having a behavior on a purification column similar to 20K hGH were selected as proteins homologous to 20K hGH in their structure. According to a homology search of amino acid sequences, TRBC (Meneewannakul, S. et al., J. Bacteriol., 173, 3872–3878, 1991) and DPPA (Periplasmic Dipeptide Transport Protein Precursor (Dipeptide-binding Protein), Olson, E. R., et al., J. Bacteriol., 173, 234–244, 1991) were selected as proteins highly homologous in their amino acid sequences. *E. coli* OppA (Periplasmic Oligopeptide Binding Protein, K. Kashiwagi et al., J. Biol. Chem., 265, 8387–8391, 1990) which was revealed by the present inventor to be similar to 20K hGH in its behavior on ion exchange columns and affinity columns was selected as a protein similar to 20K hGH in its behavior on purification columns.

Studies on the effects of secretion signals of the abovementioned three kinds of proteins on secretory production of 20K hGH showed that the amounts of 20K hGH in secretory production with the secretion signals derived from TRBC and DPPA were less than 1 mg/L, namely there was no increase in secretory production of 20K hGH. Surprisingly, however, it was revealed that the amount of 20K hGH in secretory production using E. coli OppA secretion signal was more than that for MT-10765 (FERM BP-5020) described in Japanese Patent Laid-open (Kokai) No. 322586/96 (or European Patent Publication No. 0735140).

Furthermore, the present inventors tried to further improve secretory production of 20K hGH by modifying the secretion signal derived from OppA. Results showed that the use of a secretion signal in which an appropriate number of sequences of the basic amino acid, lysin, were inserted in the positively charged region of the N terminal sequence area and an appropriate number of sequences of the hydrophobic amino acid, leucine, were inserted in the central hydrophobic region attained a secretory production of 20K hGH of more than 110 mg per 1 L culture, namely a productivity higher than that with the use of the secretion signal derived from the natural type of OppA.

It is already known and not included within the scope of present invention that the E. coli OppA secretion signal has an effective role in protein secretion in secretory production in E. coli. However, it is impossible to predict whether the modification of OppA secretion signal would be extremely effective in secretory production of 20K hGH as mentioned above from previously known information.

The present inventors examined the improvement in co-expression of proteins as s secondary trial to achieve the objectives of the present invention.

As a result, the inventors found that the use of signal peptidase 1 derived from E. coli brought secretory production of 20K hGH to a level almost equal to that achieved with the use of glutathione reductase described in Japanese Patent Laid-open (Kokai) No. 322586/96 (or European Patent Publication No. 0735140).

Moreover, surprisingly, it was revealed that the rate of impure proteins other than 20K hGH present in the periplasm solution extracted from cultured cells by an osmotic pressure shock method was extremely low in co-expression with signal peptidase 1 as compared to that in co-expression with glutathione reductase. The reason was not clear but was speculated that signal peptidase 1 strongly suppressed the stress that cells receive by 20K hGH expression, which results in a decreased tendency for lysis of culture cells and thus a reduction in contamination of cytoplasmic proteins into the periplasm extract solution. This reduction of impure proteins in the periplasm solution facilitates the purification of 20K hGH from the periplasm fraction extract solution, and thus markedly contributes to an improvement in purification efficiency and lower costs in manufacturing 20K hGH.

Signal peptidase 1 is an enzyme which cleaves a secretion signal when a precursor protein produced in the cytoplasm passes through the membrane. Jan Maarten van Dijl et al. studied the effects of excessive co-expression of signal peptidase 1 on the secretory production of beta-lactamase when it was connected to various secretion signals (Jan Maarten van Dijl et al., Mol. Gen. Genet., 227, 40–48, 1991). They reported that the effects of co-expression of signal peptidase 1 on the efficiency of processing (cleavage of signals) were different depending on the combination of secretion signal sequences in the precursor and the target protein to be secreted However, it is not at all obvious from the abovementioned report whether the co-expression of signal peptidase 1 is effective in improving the efficiency of secretion of 20K hGH, and moreover, it is not at all known that the tendency of cells to lyse is low such that the amount of impure proteins in the periplasm solution extracted from the cultured cells decreases in co-expression.

Furthermore, the present inventors altered culture conditions to determine a further improvement of secretory production of 20K hGH. As a result, the inventors succeeded in improving the production of 20K hGH up to as high as 82 mg/L by increasing the concentration of carbon source in the culture medium, using a known strain (MT-1 0765 (FERM BP-5020)) described in Japanese Patent Laid-open (Kokai) No. 32258/96 (also in European Patent Publication No. 0735140).

Accordingly, this method was further applied to MT-10852 (FERM BP-6290) and MT-10853 (FERM BP-6291) of the present invention. As a result, production was successfully increased by 4 to 5 times that of conventional production, i.e., to 350 mg/L using MT-10852 (FERM BP-6290) and to 350 mg/L using MT-10853 (FERM BP-6291), for example, with 3.5% glycerol and 1.5% succinic acid.

Further, the ratio of 20K hGH to total protein was compared, in which the ratio in a periplasm solution extracted from cells of a known strain, MT-10765 (FERN BP-5020), described in Japanese Patent Laid-open (Kokai) No. 322586/96 (or the specification of European Patent Publication No. 0735140) according to the method described in said specification is set to be 1. Results were 3.4 for MT-10853 (FERM BP-6291) in co-expression with glutathione reductase and 8.3 for MT-10852 (FERM BP-6290) in co-expression with signal peptidase 1. Thus, the productivity and purification process for 20K hGH extracted from MT-10852 (FERM BP-6290) and MT-10853 (FERN BP-6291) of the present invention was drastically improved as compared to that of the conventional method, which would enable 20K hGH production costs to be reduced.

The present invention was thus completed.

That is, the present invention comprises:

(1) a secretion signal which is more than 60% homologous to E. coli OppA secretion signal (excluding E. coli OppA secretion signal and Salmonella OppA secretion signal), (2) a DNA encoding the secretion signal in (1) above, (3) a recombinant plasmid containing a DNA fragment encoding a secretion signal having more than 60% homology to E. coli OppA secretion signal and a DNA fragment encoding a human growth hormone having a molecular weight of about 20,000, wherein the DNA encoding the human growth hormone having a molecular weight of about 20,000 is connected immediately after the DNA encoding said secretion signal, (4) a transformant transformed by the recombinant plasmid of (3) above, (5) a method of producing a human growth hormone having a molecular weight of about 20,000 characterized in that the transformant of (4) above is cultured, a periplasm fraction is extracted from the resulting cells, then the resulting periplasm fraction solution is purified to obtain a human growth hormone having a molecular weight of about 20,000, (6) A recombinant plasmid containing a DNA fragment encoding a secretion signal, a DNA fragment encoding a human growth hormone having a molecular weight of about 20,000, and a DNA fragment encoding *E. coli* signal peptidase 1, wherein the 5' end of the DNA encoding the human growth hormone having a molecular weight of about 20,000 is connected to the 3' end of the DNA encoding said secretion signal, (7) a transformant transformed by the recombinant plasmid of (6) above, (8) a method of producing a human growth hormone having a molecular weight of about 20,000 characterized in that the transformant of (7) above is cultured, a periplasm fraction is extracted from the resulting cells, then the resulting periplasm fraction solution having a small amount of impure proteins is purified to obtain a human growth hormone having a molecular weight of about 20,000.

The present invention also includes a method of increasing production by altering the medium composition in the production of a human growth hormone having a molecular weight of about 20,000 by transformants transformed by the abovementioned recombinant plasmid, namely by using a medium containing at least one of 0.01–10% glycerol and 0.01–5% succinic acid.

The present invention provides a method for secretory production of 20K hGH using *E. coli*, which enables secretory production of 20K hGH in a larger amount than conventional methods.

Figure 1:
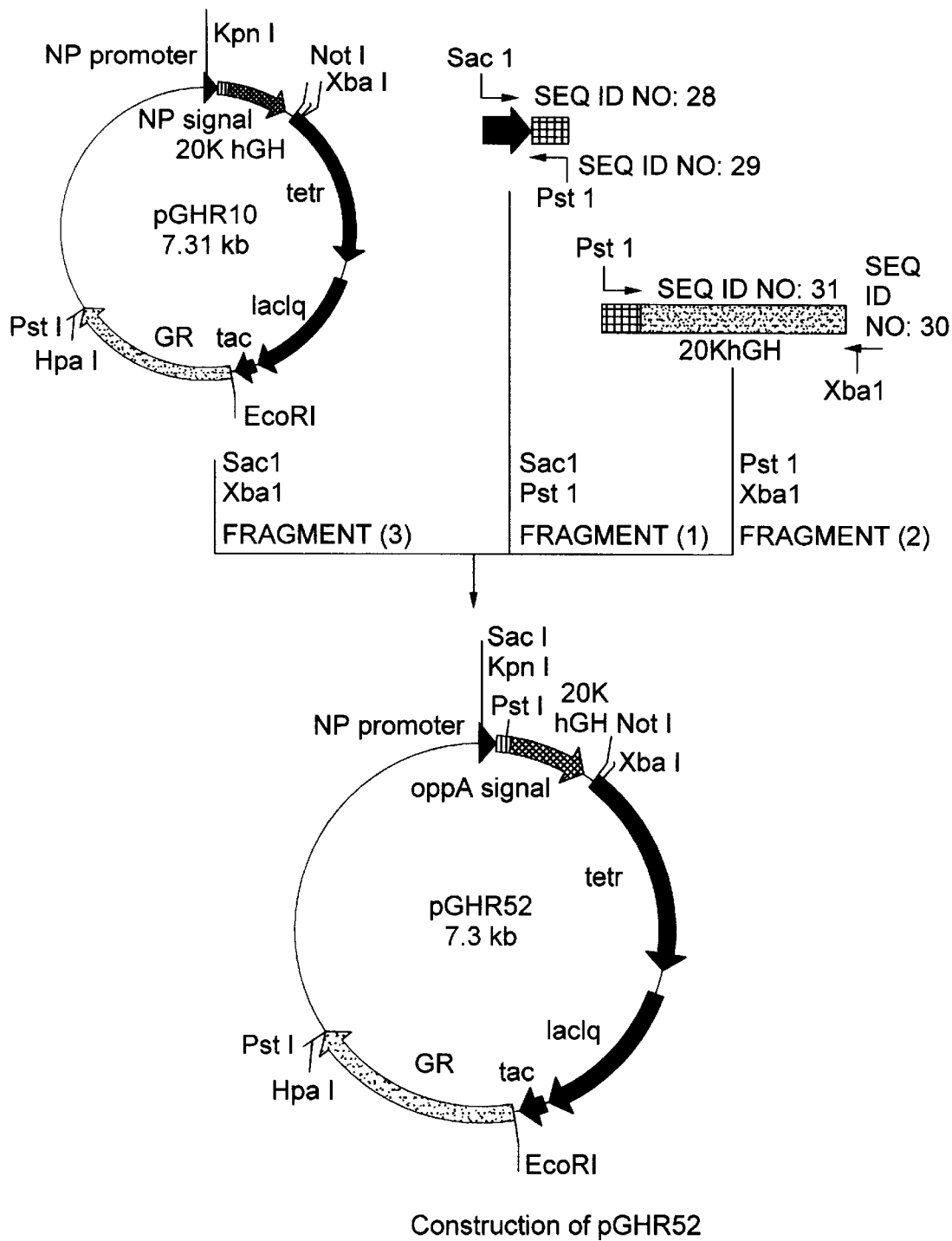
FIG. 1 shows the construction process for the 20K hGH secretion plasmid pGHR52.

Meanings of symbols in the drawings are as follows:

NP promoter: Promoter region of the neutral protease gene of Bacillus amyloliquefaciens 20K hGH: Human growth hormone having a molecular weight of about 20,000

GR: Glutathione reductase gene derived from *E. coli* tac: tac promoter region lacIq: lacIq gene tetr: Tetracycline resistance gene oppA signal: Secretion signal of *E. coli* OppA protein m-oppA signal: Modified secretion signal of *E. coli* OppA protein SPI: Signal peptidase 1 rop: rop gene derived from pBR322 ori: Origin of replication derived from pBR322.

DETAILED DESCRIPTION OF THE INVENTION AND PREFERRED EMBODIMENTS

Secretion signals to be used in the present invention include secretion signals of OppA protein of *E. coli* or Salmonella typhimurium (*E. coli* OppA secretion signal or Salmonella OppA secretion signal) and modified secretion signals in which the amino acid sequence of *E. coli* OppA secretion signal is modified so as to maintain the function as a secretion signal and more than 60% homology (modified OppA secretion signals).

*E. coli* OppA secretion signal has the amino acid sequence of SEQ ID NO: 1 in the Sequencing Listing. Examples of modified OppA secretion signals include at least one of the following modifications:

(1) insertion of 1 to 3 basic amino acids in the 2nd to 7th segment of SEQ ID NO: 1, (2) replacement of 1 to 3 acidic or neutral amino acids in the 2nd to 7th segment of SEQ ID NO: 1 with basic amino acids, (3) insertion of 1 to 9 hydrophobic amino acids at the 9th to 23rd of SEQ ID NO: 1, and (4) replacement of 1 to 9 non-hydrophobic amino acids in the 9th to 23rd segment of SEQ ID NO: 1 with hydrophobic amino acids.

Examples of the basic amino acid in the modifications in (1) and (2) include Lys and Arg and at least one of them can be used. As the hydrophobic amino acids in the modifications in (3) and (4), at least one amino acid selected from the group consisting of Leu, Ile, Val and Ala can be used.

Examples of the modified OppA signals include those having amino acid sequences of SEQ ID NOs: 2 to 27. Of these preferable modified OppA secretion signals of SEQ ID NOs: 2 to 27, the modified OppA secretion signal of SEQ ID NO: 23 is the most preferable example exhibiting the highest secretion productivity.

Salmonella OppA secretion signal has an extremely high homology to *E. coli* OppA secretion signal. Salmonella OppA secretion signal is already known and is not within the scope of the present invention. However, modified forms of Salmonella OppA secretion signal (for example, modified secretion signals having more than 60% homology in their amino acid sequence to Salmonella OppA secretion signal) are as effective as *E. coli* OppA secretion signal or modified forms thereof and thus modified Salmonella OppA secretion signals are within the scope of the present invention.

The recombinant DNA of the present invention has a structure in which the 5' end of a DNA encoding 20K hGH is directly connected to the 3' end of a DNA encoding *E. coli* or Salmonella OppA secretion signal or modified forms thereof, and can be expressed in a host to obtain a processor in which *E. coli* or Salmonella OppA secretion signal or a modified form thereof is connected to the N terminal of 20K hGH.

As the DNA encoding 20K hGH, any known DNA fragment including chemically synthesized DNA or cDNA based on the mRNA sequence of 20K hGH can be used. Furthermore, two different amino acids, serine and methionine, are reported for the 14th amino acid from the N-terminal amino acid sequence of 20K hGH. That is, Masuda, N. et al. (Biophysica Acta, 949, 125, 1988) reported that the cDNA base sequence coding for the 14th amino acid from the N terminal is AGT (a code for serine) while Martial, J. A. et al. (Science, 205, 602, 1979) reported that the RNA base sequence coding for the 14th amino acid from the N terminal of mRNA is AUG (a code for methionine). In the present invention, both DNAs coding for either amino acid can be used. Furthermore, 20K hGHs in which 1 to 5 amino acids in the amino acid sequence are replaced, deleted, lost or inserted within the range that the characteristics and functions of 20K hGH are not interfered with are also within the scope of the present invention.

The recombinant plasmid for the production of 20K hGH of the present invention can be constructed by incorporating this recombinant DNA into a plasmid such as pBR322 and pUC19 for *E. coli*, which has an origin of amplification amplifiable in the host cells in combination with a promoter which enables expression in the host cells. Any promoter can be selected, depending on the kind of host to be used, as long as it enables expression of the recombinant DNA in the host cells.

As the host, *E. coli* strains which are not pathogenic and are used ubiquitously are preferable, such as JM109, HB101 and W3110 (ATCC 27325). ATCC is an abbreviation for American Type Culture Collection.

An example of the recombinant plasmid has a promoter, a ribosome binding site, DNA encoding a secretion signal and DNA encoding 20K hGH, all connected in this order in the direction from the 5' end to the 3' end.

Signal peptidase 1 used for secretory production of 20K hGH by a co-expression system is one derived from *E. coli*. Further, the sequences in which one or two amino acids of the amino acid sequence of signal peptidase 1 derived from *E. coli* are replaced, inserted or deleted in the range that secretion of 20K hGH can be improved by co-expression as intended in the present invention are also within the scope of the present invention.

The signal peptidase 1 gene originally resides in the *E. coli* chromosome and thus the DNA encoding signal peptidase 1 derived from *E. coli* can be used. Accordingly, if *E. coli* is used as the host in the present invention, co-expression is attributed to the expression of the additional DNA which is artificially introduced besides that originating from the host.

Any promoter can be used as a promoter to express signal peptidase 1 as long as it functions in the host. Since the co-expression of signal peptidase 1 affects the level of secretion of 20K hGH, an excessive expression is not desirable. Therefore, it is preferable to use a method as as that described in the Examples, which uses lacI$^q$ to suppress the level of expression of signal peptidase 1 by the tac promoter. Furthermore, the co-expression of signal peptidase 1 can be carried out by incorporating a DNA encoding signal peptidase 1 and a DNA encoding 20K hGH into the same plasmid, incorporating a DNA encoding signal peptidase 1 and a DNA encoding 20K hGH into separate plasmids, or additionally incorporating a DNA encoding signal peptidase 1 into the *E. coli* chromosome DNA in which the signal peptidase gene naturally resides.

An example of the recombinant plasmid for co-expression constructed by incorporating a DNA encoding signal peptidase 1 and DNA encoding 20K hGH into the same plasmid has a structure in which a promoter, a ribosome binding site, a DNA encoding a secretion signal, a DNA encoding 20K hGH, a promoter and a DNA encoding signal peptidase 1 are connected in this order in the direction from the 5' end to the 3' end.

Any secretion signal which enables the secretion of 20K hGH can be used as a secretion signal to be incorporated into a recombinant plasmid for the co-expression system. Preferable examples include the abovementioned *E. coli* or Salmonella OppA secretion signal or modified forms thereof. The abovementioned DNA encoding 20K hGH and the promoter, the origin of replication and the like for the expression of DNA can also be used in this system.

The *E. coli* transformant of the present invention can be obtained by incorporating the abovementioned recombinant plasmid into a host by a known method. The host is transformed readily by the recombinant plasmid by an ordinary method, for example, by a method in which a competent cell is prepared by the rubidium chloride method, the resultant competent cell and the plasmid are mixed, then the mixture is subjected to heat shock at 42C for 1 minute for incorporation of the plasmid into the host cell.

In the resulting transformant, a precursor in which the secretion signal and 20K hGH are connected is expressed under the control of the promoter and ribosome binding site sequence in the cytoplasm, the secretion signal is cleaved by signal peptidase 1 when this precursor passes through the inner membrane, then natural-type 20K hGH is secreted. When *E. coli* is used as the host, the natural-type 20K hGH is secreted and accumulated in the periplasm of *E. coli*.

Examples of the *E. coli* transformant of the present invention for secretory production of 20K hGH include MT-10853 (FERM BP-6291) and MT-10852 (FERM BP-6290). These strains are deposited with the abovementioned accession numbers according to the Budapest Treaty for International Agreement on Deposition of Microorganisms for Patent Procedure at the National Institute of Bioscience and Human-Technology of the Agency of Industrial Science and Technology of the Ministry of International Trade and Industry (1–3 Higashi 1-Chome, Tsukuba-shi, Ibaraki Prefecture).

*E. coli* transformants for secretory production of 20K hGH using *E. coli* as a host can be appropriately cultured in a flask or in a jar fermenter. The culture temperature is preferably 25–37C, more preferably 28–30C. Any medium used for an ordinary culture of *E. coli* can be used. A preferable culture medium is a 2-fold concentrated LB medium (20 g/L polypeptone, 10 g/L yeast extract) supplemented with 0.01–10%, preferably 0.1–5%, glycerol, and 0.01–5%, preferably 0.1–4%, more preferably 0.1–3%, succinic acid. The supplemented effect of glycerol and succinic acid is remarkable when added in combination. However, the effect was also found when either glycerol or succinic acid is added by itself.

The 20K hGH from *E. coli* transformants can be readily prepared by an ordinary method of extracting and purifying proteins from the periplasm. For example, an osmotic pressure shock method (Nossal G.N., J. Biol. Chem., 241(13), 3055–3062, 1966) can be used. The extracted periplasm fraction can be purified by an ordinary method of purifying proteins, for example, a column chromatography method. In an ion exchange column chromatography method in which proteins first have to be loaded onto a carrier, the volume of the column can be advantageously small in the present invention because the periplasm liquid fraction contains a low level of impure proteins other than 20K hGH.

The present invention will be illustrated in detail by the following examples; however, the invention is not intended to be limited to these examples.

EXAMPLE 1

Study on Usefulness of OppA Secretion Signal

[1] Construction of 20K hGH secretion plasmid containing OppA secretion signal gene Oligonucleotides of SEQ ID NO: 28 and SEQ ID NO: 29 were made into double stranded chains by PCR (Polymerase Chain Reaction ) and the resulting chains were cleaved with restriction endonucleases SacI and PstI to obtain a DNA fragment (1) encoding the promoter derived from Bacillus amyloliquefaciens neutral protease and the front-half of OppA secretion signal. Using secretion plasmid pGHR10 derived from strain MT-10765 (FERM BP-5020) described in Japanese Patent Laid-open (Kokai) No. 322586/96 as a template, a DNA fragment encoding the back-half of OppA secretion signal and 20K hGH was amplified by PCR using primers of SEQ ID NO: 30 and SEQ ID NO: 31. The resultant PCR product was cleaved with restriction enzymes PstI and XbaI to obtain a DNA fragment (2). Further, secretion plasmid pGHR10 was cleaved with restriction enzymes SacI and XbaI to obtain a vector-side fragment (3). These DNA fragments (1), (2) and (3), were ligated to construct secretion plasmid pGHR52. The process for these steps is shown in FIG. 1.

Figure 2:
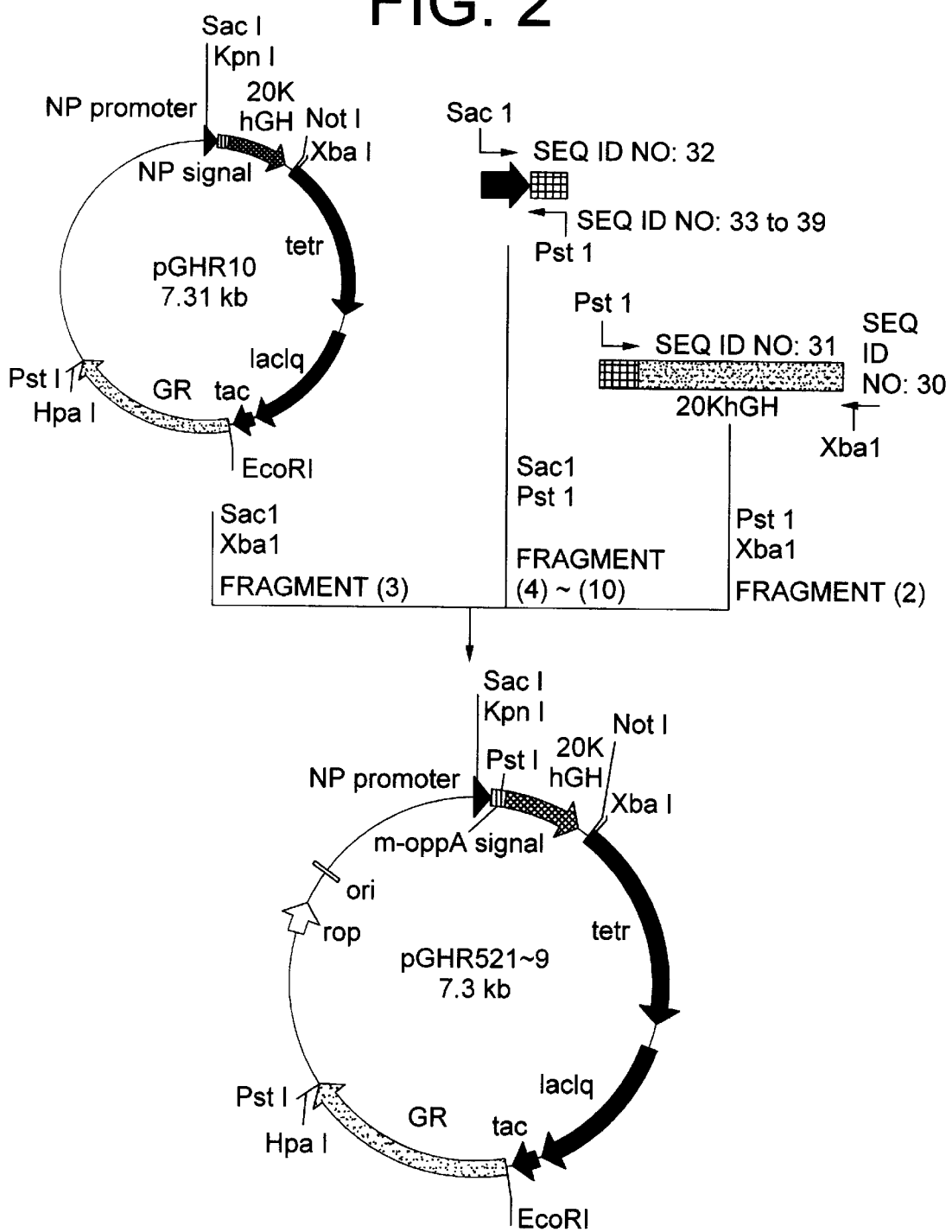
FIG. 2 shows the construction process for the 20K hGH secretion plasmids pGHR521–529.

[2] Construction of 20K hGH Secretion Plasmid Containing Modified OppA Secretion Signal Gene Using pGHR52 constructed in [1] as a template, a DNA fragment encoding the promoter derived from neutral protease of Bacillus amyloliquefaciens and a modified part of OppA secretion signal was amplified by PCR selectively using the oligonucleotide of SEQ ID No: 32 and various oligonucleotides of SEQ ID NOs: 33–39. The resulting PCR products were cleaved with restriction enzymes SacI and PstI to obtain fragments (4), (5), (6), (7), (8), (9) and (10). Next, the abovementioned fragments (2) and (3) and fragment (4) were mixed and ligated, then used for the transformation of E. coli cells (namely, fragment (4) is used in place of fragment (1) in FIG. 1) to obtain secretion plasmid pGHR521. Similarly, secretion plasmid pGHR523 was obtained using fragment (5) in place of fragment (4), and secretion plasmids pGHR525, pGHR527, pGHR529, pGHR524 and pGHR526 were obtained using fragments (6), (7), (8), (9) and (10) in place of fragment (1), respectively (FIG. 2).

[3] Evaluation of E. coli Transformants Transformed by 20K hGH Secretion Plasmid Containing OppA Secretion Signal Gene Cells of E. coli W3110 strain (ATCC 27325) were transformed by secretion plasmid pGHR52 constructed in [1] to obtain an E. coli transformant strain, W3110/pGHR52.

Cells of this transformant strain were cultured on an LB agar medium supplemented with 10 μg/ml tetracycline at 30° C. for 18 hours. The resultant cells were cultured in a liquid medium (20 g/L polypeptone, 10 g/L yeast extract, 10 g/L succinic acid, 10 g/L glycerol and 30 mg/L tetracycline) at 30° C. for 24 hours. After culturing, a periplasm fraction containing secreted and accumulated 20K hGH was recovered from the cells by the osmotic shock method, and the 20K hGH concentration in the periplasm fluid fraction was measured by enzyme-immunoassay using an antibody against the human growth hormone. The amount of secreted 20K hGH per one liter of culture was calculated from the measurement. To compare the amount of secretory production, cells of MT-10765 (FERM BP-5020) were similarly cultured. Results are shown in Table 1.

TABLE 1

Difference in the amount of 20K hGH in secretory production using different secretion signals

| Plasmid | pGHR10 | pGHR52 |
|---|---|---|
| Secretion signal | Derived from Bacillus amyloliquefaciens neutral protease (modified form) | Derived from E. coli OppA |
| Production (mg/L) | 76 | 89 |

Results shown in Table 1 revealed that the E. coli transformant transformed by the plasmid carrying OppA secretion signal gene is superior to the E. coli transformant transformed by the plasmid carrying the gene for the modified secretion signal derived from B. amyloliquefaciens neutral protease in secretory production of 20K hGH.

[4] Evaluation of E. coli Transformants Transformed by Plasmids Carrying the Genes for Modified OppA Secretion Signals Cells of E. coli W3110 strain (ATCC 27325) were transformed by secretion plasmids constructed in [2] to obtain E. coli transformant strains. Cells of resulting transformants were cultured as described in [3] and the amount of secretion was similarly measured. Results are shown in Table 2.

TABLE 2

Difference in secretion of 20K hGH with various modified OppA secretion signals

| Plasmid | Production (mg/L) |
|---|---|
| pGHR521 | 89 |
| pGHR523 | 100 |
| pGHR524 | 115 |
| pGHR525 | 120 |
| pGHR526 | 108 |
| pGHR527 | 90 |
| pGHR529 | 89 |

Results shown in Table 2 revealed that the E. coli transformants transformed by the plasmids carrying the genes for modified OppA secretion signals were superior to the conventional E. coli transformant transformed by the plasmid carrying the genes for the modified secretion signals derived from B. amyloliquefaciens neutral protease in secretory production of 20K hGH. In particular, E. coli transformant MT-10853 (FERM BP-6291) transformed by pGHR525 carrying the gene for modified OppA secretion signal of SEQ ID NO: 3 showed the greatest secretory productivity.

EXAMPLE 2

Study on Usefulness of Signal Peptidase 1

Figure 3:
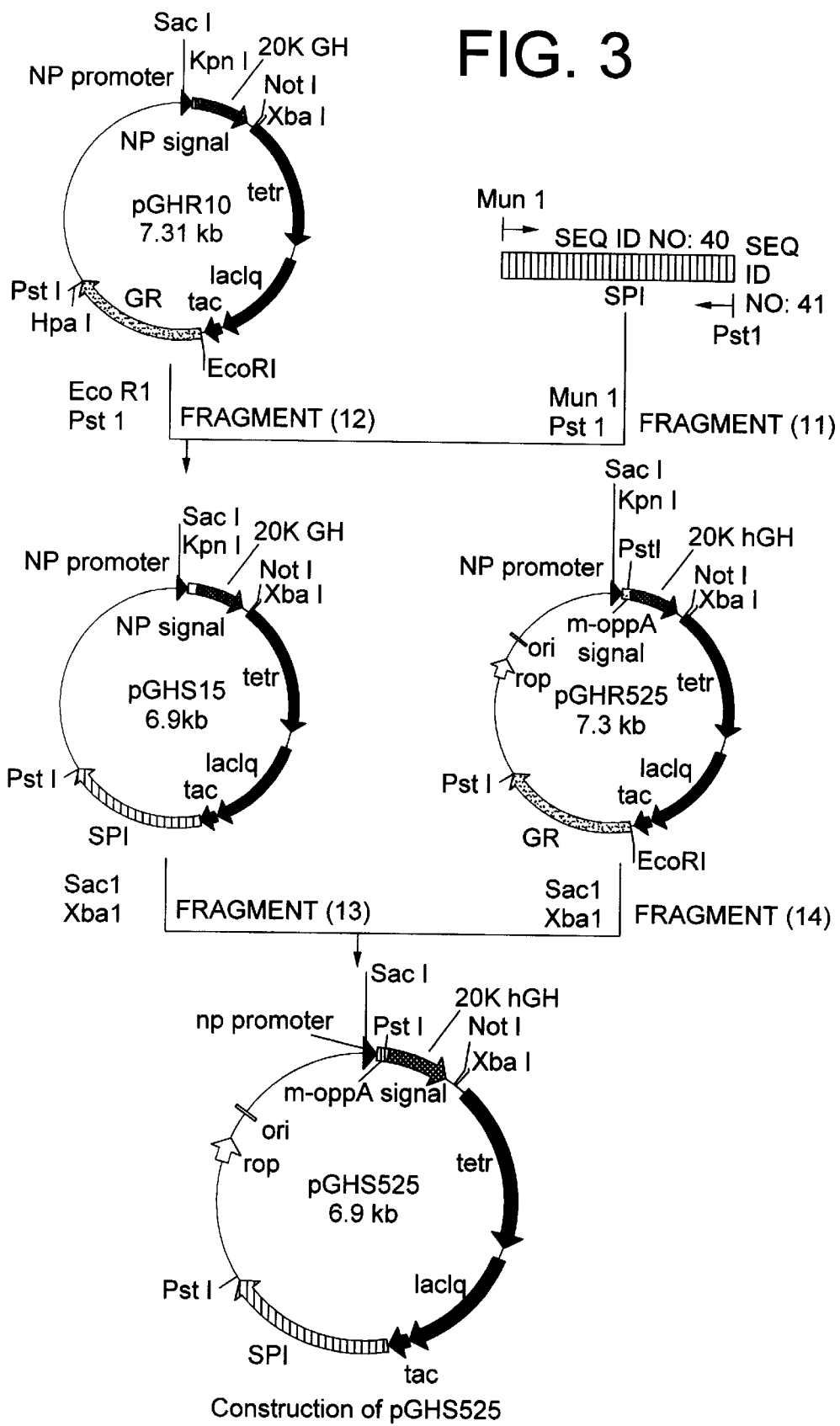
FIG. 3 shows the construction process for the 20K hGH secretion plasmid pGHS525.

[1] Construction of 20K hGH Secretion Plasmid for Co-Expression of Signal Peptidase 1 Using Modified OppA Secretion Signal From the chromosomal gene of E. coli W3110, a DNA fragment encoding signal peptidase 1 was amplified by PCR using oligonucleotides of SEQ ID NO: 40 and SEQ ID NO: 41. The resultant PCR product was cleaved with restriction enzymes MunI and PstI to obtain a DNA fragment encoding signal peptidase 1 (11). This fragment (11) and a vector side fragment (12) which was created by cleaving pGHR10 described in Japanese Patent Laid-open (Kokai) No. 322586/96 with restriction enzymes EcoRI and PstI were mixed and ligated by an ordinary method, then used for transformation of E. coli W3110 (ATCC 27325) to obtain secretion plasmid pGHS15 (FIG. 3). The resulting pGHS15 was cleaved with restriction enzymes SacI and XbaI to obtain a vector side fragment (13). Further, recombinant plasmid pGHR525 obtained in Example 1 was cleaved with restriction enzymes SacI and XbaI to obtain a 20K hGH expression cassette side fragment (14). Then, fragment (13) and fragment (14) were mixed and ligated to obtain secretion plasmid pGHS525 (FIG. 3). This plasmid was used to transform E. coli W3110 strain to obtain transformant W3110/pGHS525 (MT-10852 (FERM BP-6290)).

[2] Evaluation of E. coli transformant transformed by plasmid carrying DNA for signal peptidase 1

Cells of transformant W3110/pGHS525 strain constructed in [1] were cultured in the same manner as described in Example 1 [3] and the amount of secreted 20K hGH was measured. The amounts of the total protein in periplasm fractions recovered from culture fluids of W3110/pGHR10, W3110/pGHR525 and W3110/pGHS525 by the method described in Example 1 [3] were measured by the method of Groves et al (Groves, W. E. et al., Anal. Biochem., 22, 195–210,1968), and a comparison was made by setting the ratio of 20K hGH to the total protein in the periplasm fraction for W3110/pGHR10 as 1. Results are shown in Table 3.

TABLE 3

Effect of use of signal peptidase 1 on secretory production of 20K hGH

| Plasmid | pGHR10 | pGHR525 | pGHS525 |
|---|---|---|---|
| Production (mg/L) | 76 | 110 | 115 |
| Ratio of 20K hGH to total protein in periplasm extract fluid fraction culture | 1 | 1.6 | 4.8 |

Results shown in Table 3 revealed that the level of secretory production of 20K hGH by the *E. coli* transformants transformed with the recombinant plasmid, in which signal peptidase 1 was co-expressed, was higher than that by the transformants transformed with the conventional plasmid in which glutathione reductase was co-expressed, and the ratio of 20K hGH to the total protein in the periplasm extract fluid solution was greatly improved.

Example 3

Evaluation of 20K hGH productivity in altered culture conditions

Cells of *E. coli* transformants W3110/pGHR525 (MT-10853 (FERM BP-6291)) constructed in [4] of Example 1 and W3110/pGHS525 (MT-10852 (FERM BP-6290)) and the known strain W3110/pGHR10 (MT-10765 (FERM BP-5020)) described in Japanese Patent Laid-open (Kokai) No. 322586/96 (or European Patent Publication No. 0735140), for comparison, were cultured in an altered medium and the resultant cultures were evaluated.

Cells of each transformant strain were cultured on an LB agar medium supplemented with 10 μg/ml tetracycline at 30° C. for 18 hours. The resultant cells were cultured in a liquid medium (20 g/L polypeptone, 10 g/L yeast extract, 15 g/L succinic acid, 36 g/L glycerol and 30 mg/L tetracycline) at 30° C. for 42 hours. After culturing, the periplasm fraction containing secreted and accumulated 20K hGH was recovered from the cells by the osmotic pressure shock method, and the 20K hGH concentration in the periplasm fluid fraction was measured by enzyme-immunoassay using an antibody against the human growth hormone. The amount of secreted 20K hGH per one liter of culture fluid was calculated from the measurement. The amount of the total protein in each periplasm fraction was measured by the method of Groves et al. (Groves W. E. et al., Anal. Biochem., 22, 195–210,1968). The ratio of 20K hGH to the total protein in the periplasm fraction for W3110/pGHR10, which was cultured and extracted for periplasm fraction by the method described in [3] of Example 1, was set to be 1. Results are shown in Table 4.

TABLE 4

20K hGH production and ratio of 20K hGH to the total protein in the periplasm fluid extract in the altered medium composition

| Strain | W3110/ pGHR10 | W3110/ pGHR10 | W3110/ PGHR525 | W3110/ pGHS525 |
|---|---|---|---|---|
| Glycerol | 10 g/L | 36 g/L | 36 g/L | 36 g/L |
| Succinic acid | 10 g/L | 15 g/L | 15 g/L | 15 g/L |
| 20K hGH production | 76 mg/L | 82 mg/L | 350 mg/L | 360 mg/L |
| Ratio of 20K hGH to the total protein in periplasm fraction | 1 | 1.1 | 3.4 | 8.3 |

The present invention provides a method for secretory production of 20K hGH using *E. coli* cells, in which the level of secretory production of 20K hGH is higher than that attained by a conventional method.

Furthermore, the level of impure proteins in the periplasm extract solution obtained according to the present invention is low so that 20K hGH can be readily purified from the extract, therefore large amounts of highly pure 20K hGH can be produced at low cost.

Production efficiency of 20K hGH can be further improved by using a medium containing at least one of 0.01–10% glycerol or 0.01–5% succinic acid.

What is claimed is:

1. An isolated secretion signal which is different from *E. coli* or Salmonella OppA secretion signals but is more than 60% homologous to said *E. Coli* OppA secretion signal in its amino acid sequence, characterized in that when the secretion signal is expressed as a fusion protein to the 20,000 kd human growth hormone a human growth hormone having a molecular weight of about 20,000 can be secreted and produced using a microorganism having a recombinant DNA in which the 3' end of a DNA encoding said secretion signal is operatively linked to the 5' end of a DNA encoding the human growth hormone having a molecular weight of about 20,000.

2. An isolated secretion signal which is more than 60% homologous to said *E. coli* OppA secretion signal in its amino acid sequence according to claim 1, wherein said secretion signal includes at least one of the following modifications of the sequence in the amino acid sequence of SEQ ID NO: 1

(1) insertion of 1 to 3 basic amino acids in the $2^{nd}$ to $7^{th}$ amino acid of SEQ ID NO: 1, (2) replacement of 1 to 3 acidic or neutral amino acids in the $2^{nd}$ to $7^{th}$ amino acid of SEQ ID NO: 1 with basic amino acids, (3) insertion of 1 to 9 hydrophobic amino acids in the $9^{th}$ to $23^{rd}$ amino acid of SEQ ID NO: 1, and (4) replacement of 1 to 9 non-hydrophobic amino acids in the $9^{th}$ to $23^{rd}$ amino acid of SEQ ID NO: 1 with hydrophobic amino acids.

3. An isolated secretion signal according to claim 2 wherein the basic amino acids to be inserted or to be replaced in the $2^{nd}$ to $7^{th}$ amino acid of SEQ ID NO: 1 are selected from Lys and Arg and the hydrophobic amino acids to be inserted or replaced in the $9^{th}$ to $23^{rd}$ amino acid of SEQ ID NO: 1 are amino acids selected from the group consisting of Leu, Ile, Val and Ala.

4. An isolated secretion signal according to claim 3 having the amino acid sequence of any one of SEQ ID Nos: 2 to 27.

* * * * *